US006418344B1

(12) United States Patent
Rezai et al.

(10) Patent No.: US 6,418,344 B1
(45) Date of Patent: Jul. 9, 2002

(54) METHOD OF TREATING PSYCHIATRIC DISORDERS BY ELECTRICAL STIMULATION WITHIN THE ORBITOFRONTAL CEREBRAL CORTEX

(75) Inventors: Ali R. Rezai; Brian H. Kopell, both of New York City, NY (US)

(73) Assignee: ElectroCore Techniques, LLC, Summit, NJ (US)

( * ) Notice: Subject to any disclaimer, the term of this patent is extended or adjusted under 35 U.S.C. 154(b) by 0 days.

(21) Appl. No.: 09/511,843

(22) Filed: Feb. 24, 2000

(51) Int. Cl.[7] .............................. A61N 1/18; A61N 1/36
(52) U.S. Cl. ......................................................... 607/45
(58) Field of Search ........................................ 607/3, 45

(56) References Cited

U.S. PATENT DOCUMENTS

| | | | | |
|---|---|---|---|---|
| 5,938,688 A | * | 8/1999 | Schiff | 607/45 |
| 6,128,537 A | * | 10/2000 | Rise | 607/45 |
| 6,167,311 A | * | 12/2000 | Rezai | 607/45 |
| 6,263,237 B1 | * | 7/2001 | Rise | 607/3 |

\* cited by examiner

Primary Examiner—Carl Layno
(74) Attorney, Agent, or Firm—Joseph P. Errico; Timothy J. Bortree

(57) ABSTRACT

A method for treating psychiatric diseases such as Anxiety disorder (including General Anxiety Disorder, Obsessive Compulsive Disease, and Panic Disorder), Affective Disorder(including Major Depression and Bipolar Disorder) by neuromodulation (either chemical or electrical) of the frontal cerebral cortex, and in particular regions within the orbitofrontal cerebral cortex. The method includes the steps of determining a common group of patients, each suffering from a common specific diagnosis for a psychiatric disorder; determining which common regions of the patients' orbitofrontal cerebral cortex are involved in the pathogenesis of the abnormal electrical and chemical activity associated with the psychiatric disease; surgically implanting an electrode and/or catheter and electrical signal generating device and/or drug-delivery pump such that the electrode and/or catheter is positioned within the region of the frontal cerebral cortex known as the orbitofrontal cortex; and selectively adjusting the level of electrical and/or chemical stimulation in accordance with the specific effect of the stimulation of the patient. In particular, the region of the frontal cerebral cortex most frequently associated with psychiatric disorders is the orbitofrontal cortex.

5 Claims, 5 Drawing Sheets

METHOD OF TREATING PSYCHIATRIC DISORDERS BY ELECTRICAL STIMULATION WITHIN THE ORBITOFRONTAL CEREBRAL CORTEX

BACKGROUND OF THE INVENTION

1. Field of the Invention

This invention relates generally to the treatment of psychiatric disorders by modulating the activity within appropriate regions of the cerebral prefrontal cortex, and more particularly to a method of modifying pathological electrical and chemical activity of the brain by electrical stimulation and/or direct placement of neuromodulating chemicals within the corresponding areas of the orbitofrontal cerebral cortex (OFC).

2. Description of the Prior Art

The treatment of psychiatric disorders by neurosurgical techniques has an extensive history. In the early 1930's Fulton and Jacobsen first recongnized that an experimentally induced neurotic behavior in chimpanzees could be abolished by frontal lobectomy. Within a few years, Freeman and Watts developed the first psychosurgical procedure for humans known as the frontal lobotomy. As the inherent physiology of the frontal lobe became more evident, the original freehand procedure of Freeman and Watts became less and less extensive. By the late 1940's, the method of stereotaxis, in which the patient's brain is modeled in 3-dimensional space for exquisite targeting accuracy, merged with lesioning techniques resulting in an even more efficacious and safe psychosurgical procedure. Further developments of stereotactic equipment have combined with novel advancements in functional and anatomic imaging to encompass the state of the art in the neurosurgical treatment of psychiatric disorders today. However, the fundamental limitation of these lesioning techniques is that they are inherently irreverible and static in nature. There is no proverbial "off" switch to alleviate side effects and no way to adjust the desirable effects in response to a patient's developing symptom profile.

Within the field of neurosurgery, the use of electrical stimulation for treating neurological disease, including such disorders as compulsive eating, chronic pain, movement disorders, has been widely discussed in the literature. It has been recognized that electrical stimulation holds significant advantages over alternative methods of treatment, for example lesioning, inasmuch as lesioning can only destroy neuronal activity. In many instances, the preferred effect is to stimulate or reversibly block neural signals. Electrical stimulation permits such stimulation of the target neural structures, and equally importantly, it does not require the destruction of the nervous tissue (it is a reversible process, which can literally be shut off or removed at will).

Another technique which offers the ability to affect neuronal function in a reversible and dynamic fashion is the delivery of drugs directly to target tissues via a subcutaneously implanted pump. Such drugs, either traditional psychiatric agents or chemicals mimicking neurotransmitters, could be instilled at such low doses as to completely avoid the side effects so common to moden pharmacotherapy. Such doses could also be tailored in magnitude with regard to a particular patient's varying symptomatology. A chemical neuromodulating system could be implanted as a primary treatment strategy or in combination with an electrically based one. A combination therapeutic approach, one combining electrical and chemical means, would be penultimate to generating healthy neuronal tissue itself.

To date, however, disorders manifesting gross physical dysfunction, not otherwise determinable as having emotional or psychiatric origins, comprise the vast majority of those pathologies treated by deep brain stimulation. A noteworthy example of treatment of a gross physical disorder by electrical stimulation is included in the work of Alim Benabid, and his research team, who have proposed a method of reducing, and in some cases eliminating, the temor associated with Parkinson's disease by the application of a high frequency electrical pulse directly to the subthalamic nucleus (see Neurosurgical Operative Atlas, Vol. 8, March 1999, pp. 195–207, Chronic Subthalamic Nucleus Stimulation For Parkinson's Disease; and New England Journal of Medicine, Vol. 339, October 1998, pp. 105–1111, Electrical Stimulation of the Subthalamic Nucleus in Advanced Parkinson's Disease).

Conversely, direct neuroaugmentation treatments for disorders which have traditionally been treated by behavioral therapy or psychiatric drugs, has been largely limited to the stereotactic lesioning procedures mentioned above. The four lesioning techniques mostly in use today are cingulotomy, capsulotomy, subcaudate tractotomy, and limbic leucotomy. Such procedures have been applied to date in the treatment of Affective disorders and Anxiety disorders. If one critically examines the results of these procedures in the literature, it would be apparent, when applied to a carefully selected patient population in conduction with modern equipment and imaging techniques, these procedures are both efficacious and safe. In fact, in a certain subset of patients who have failed all conventional (pharmacotherapy and psychotherapy) treatments, these neurosurgical procedures are the only efficacious options available. If would follow that electrical and/or chemical neuromodulating techniques with their inherent reversibility and adjustability would an even better solution than the traditional lesioning techniques. To date, however, intracranial neuromodulation techniques have been largely unexplored. Only recently, in the Oct. 30, 1999 issue of Lancet, have Meyerson et al. described a technique for deep brain electrical stimulation of the anterior internal capsule for OCD patients. While the results are preliminary, they are also quite promising as three of the four patients had good results.

Another effort has been made to treat psychiatric disorders via peripheral nerve stimulation. A noteworthy example is the effort to control compulsive eating disorders by stimulation of the vagus nerve which has been described by Wernicke, et al. in U.S. Pat. No. 5,263,480. This treatment seeks to induce a satiety effect by stimulating the afferent vagal fibers of the stomach. For patients having weak emotional and/or psychological components to their eating disorders, this treament can be effective insofar as it eliminates the additional (quasi-normal) physio-chemical stimulus to continue eating. This is especially true for patients who exhibit subnormal independent functioning of these fibers of the vagus nerve. For compulsive eating patients who are not suffering from an insufficient level of afferent vagal nerve activity resulting from sufficient food intake, however, the over stimulation of the vagus nerve and potential resultant over abundance of satiety mediating chemicals (cholecystokinin and pancreatic glucagon) may have little effect. It has even been suggested that continued compulsive eating, despite overstimulation of the vagus nerve, may exacerbate the emotional component of the patient's disorder. This, therefore, begs the question, is vagus nerve stimulation useful in treating the psychological component of the disorder of compulsive eating, or is it simply a method of minimizing the additional, but natural, pressures to eat because of normal physical hunger. More generally, the question may be asked, is peripheral nerve stimulation of any kind the most appropriate method of treatment for disorders which are, at the core, the result of a pathology exhibited in the brain.

If the answer to this question is that the stimulation of a peripheral nerve can result in the release of a chemical which specifically counteracts the psychological pathology, for example if the release of greater amounts of cholecystokinin and pancreatic glucagon had a direct effect on the pathology exhibited in the brain, then, for that patient, the treatment will have a greater probability of success. If, however, as is most probably the case, the increase in the level of activity of the peripheral nerve does not result in the release of such a chemical, and therefore, has no effect on the area of the brain responsible for the emotional/psychiatric component of the disorder, then the treatment will have a much lower probability of success.

The impetus, therefore, would be to treat Psychiatric disorders with direct modulation of activity in that portion of the brain causing the pathological behavior. In some manner, however, the determination of what regions of the brain are exhibiting pathological function must be determined. Fortunately, several methods for determining precisely this have been developed by a number of researchers.

Normal brain function can be characterized by four discrete frequencies of electrical output Other frequencies are almost exclusively associated with pathology. The use of magnetoencephalography (MEG scans) has permitted quantificaion of electrical activity in specific regions of the brain. It has been proposed that MEG scans may be used to identify regions exhibiting pathological electrical activity. The resolution of the MEG scans of the brain are highly accurate (sub-one millimeter accuracy), however, correlating the MEG scan with MRI images for the surgical purposes of identifying anatomical structures limits the overall resolution for surgical purposes to a volume of 10 to 30 cubic millimeters. Other techniques focus on the metabolic changes that occur in the extracellular milieu in response to neural acitivity. Such techniques include functional magnetic resonance imaging (FMRI) and positron emission tomography (PET). While such techniques lack the temporal and spatial resolution of MEG, they are able to observe activity that is sometimes unable to be seen by MEG (due to the inherent nature of the technique).

From its earliest inception, the neurosurgical approach towards the treatment of Anxiety and Affective disorders has centered around the frontal cerebral cortex. Indeed, as Freeman and Watts' forntal lobotomy evolved, the areas of surgical intervention focused more and more on the OFC. Neurosurgeons, neurologists, and psychiatrists have found that intervention in this area afforded the most efficacious procedure while minimizing the effect on other unwanted areas. The frontal cerebral cortex based on clinical, neuropsychological, and functional imaging studies has been shown to be involved in cognitive integration and planning, features generally considered specific to the human intellect. More specifically, these studies have shown that the OFC is involved with the integration of the emotional state on the above processes. Furthermore, the OFC has been demonstrated to be involved with the internal representation of reward with regard to task completion. In laymans terms, the OFC helps mediate the feeling of accomplishment one feels when an internally generated task is completed. Neuropsychological and functional neuroimaging studies have all implicated the OFC in the pathogenesis of Affective, Anxiety, and Substance Abuse disorders. Given these findings, it is not surprising that three of the four stereotactic procedures currently in use for the treatment of Affective and Anxiety disorders (capsulotomy, subcaudate trachtotomy, and limbic leucotomy) seek to alter the output and/or input of the OFC. Taken one step further, the OFC appears to be an ideal place for the reversible and dynamic neuromodulation techniques described herein.

It is therefore the principal object of the present invention to provide a more generically applicable method for treating certain psychiatric disorders.

It is further an object of the present invention to provide a fully reversible and adjustable method of treating certain psychiatric disorders.

It is still further an object of the present invention to provide a method of treating certain psychiatric disorders the effectiveness of which may be evaluated rapidly.

It is also an object of the present invention to provide a method of interventionally treating certain psychiatric disorders while minimizing the necessary pathological investigaion.

SUMMARY OF THE INVENTION

The preceding objects are provided in the present invention, which comprises new and novel methods of treating psychiatric disorders by implantation of stimulation electrodes and/or intra-axial drug delivery catheters at specific locations in the frontal cerebral cortex. In another aspect, the present invention also comprises new and novel methods for identifying the proper positioning of the electrodes/and or catheters within the frontal cerebral cortex for a given specific psychiatric disorder. More particularly, in the first aspect, the present invention comprises a method of therapeutically treating a psychiatric disorder by surgically implanting an electrode and/or drug delivery catheter into a predetermined site within the brain of the patient, wherein the predetermined site is selected within the prefrontal cortex. Referring more particularly to FIG. 1, the orbitofrontal cerebral cortex 12 consists of a subsection of the frontal cerebral cortex 10, the most anterior portion of the brain. Specifically, the orbitofrontal cortex 12 lies medially to the inferior frontal gyrus 14 and lateral to the gyrus rectus. The orbitofrontal cortex (OFC) is also distinct cytotechtonically, corresponding to areas 10 and 11 according to the widely accepted classification scheme of Brodmann. In FIG. 2, the anatomic connections of the OFC with dorsomedial and anterior thalamic nucleii, the striatum, the pallidum, and the Papez circuit (which is thought to mediate emotional affect in man) are illustrated in a conceptual map.

The OFC has direct and reciprocal excitatory connections, presumably mediated by the neurotransmitter glutamate, with the dorsomedial and anterior thalamic nucleii. In addtion, a more indirect loop exists between the OFC, the dorsomedial thalamic nucleus, the ventromedial striatum, and the globus pallidus. Multiple connections also exist between the OFC and the limbic system. The limibc system is a group of structures in the brain which are thought to mediate the emotional state. At the core of this system is the Papez circuit, first illustrated in 1937, which includes the cingulate gyrus, the anterior thalamic nucleus, the amygdala, the fornix, and the mamillary bodies. The OFC has numerous connections with the Papez circuit via the baslolateral amygdala, the anterior thalmic nucleus and the anterior cingulate gyrus.

In the first aspect of the invention, therefore, the proximal end of the electrode and/or catheter is coupled to an electrical signal source and/or drug delivery pump which, in turn, is operated to stimulate the predetermined treatment site in the orbitofrontal cortex of the brain, such that the clinical effects of the psychiatric disorder are reduced.

In the second aspect, the present invention comprises a method of determining the proper therapeutic treatment, i.e., the proper position or placement of the electrodes and/or catheters, for a specific psychiatric disorder comprising the steps of identifying a large sampling of patients, each exhibiting a common specific psychiatric disorder and then identifying which common region of the orbitofrontal cortex exhibits pathological electrical and/or chemical activity during manifestations of the specific psychiatric disorder. The common regions demonstrating this pathological activity constitute the predetermined treatment site, whereafter a suitable means for affecting the activity of said predetermined treatment site may be employed to ameliorate the psychiatric disorder generically with a high probability of success.

In particular, the region identified above, including the orbitofronal cortex, is herein identified by its known anatomical connections and functional brain imaging as being actively involved in channeling or generating the pathological electrical activity associated with psychiatric disorders. It is important to note that this region, its functions, and its connections is a common structural feature of human brains, and therefore is a common target across a large number of patients. As suggested above, this commonality of function and structure within the orbitofrontal cortex allows for common treatment targeting, even in instances wherein different patients have other disparate locations within their brains that also exhibit pathological electrical activity.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

The present invention comprises a method of identifying and treating patients who suffer from certain known psychiatric disorders. As suggested by this introductory statement, the specific steps involved with this method comprise two separate stages: first, the identification of patients and the preparation for surgical intervention; and second, the actual surgical procedure.

With respect to the first of these stages, that is the pre-operative steps, the identification of suitable patients begins with the accumulation of physical, chemical, and historical behavioral data on each patient. A collection of patients who have been identified as exhibiting similar clinical symptoms are then grouped together and subject to a series of common non-invasive brain imaging studies. These brain imaging studies are intended to identify the regions of the brain, and more particularly, the regions of the orbitofrontal cortex, which exhibits clinically recognizable deviation from normal electrica and/or metabolic activity. Several diagnostic tools are useful in this capacity, including fluoro-deoxyglucose-positron-emission tomography (FDG-PET), electro-encephalography (EEG), magnetic resonance imaging (MRI), and magnetoencephelagraphy.

In the present invention, psychiatric disorders such as Affective disorder (including Major Depression and Bipolar Disorder), Anxiety disorder (including General Anxiety Disorder, Obsessive Compulsive Disorder, and Panic Disorder) and Substance Abuse Disorder are identified as having a probable commonality in frontal lobe activity associated with the orbitofrontal cortex. Therefore, once a patient has been identified as exhibiting abnormal clinical behavior symptomatic of one of these disorders, subsequent pre-operative brain imaging scans are used to support the presumption that the abnormal signals associated with the disorder are being associated with this region of the frontal cerebral cortex, and then surgical intervention with electrical and/or chemical stimulation is taken.

Figure 1:
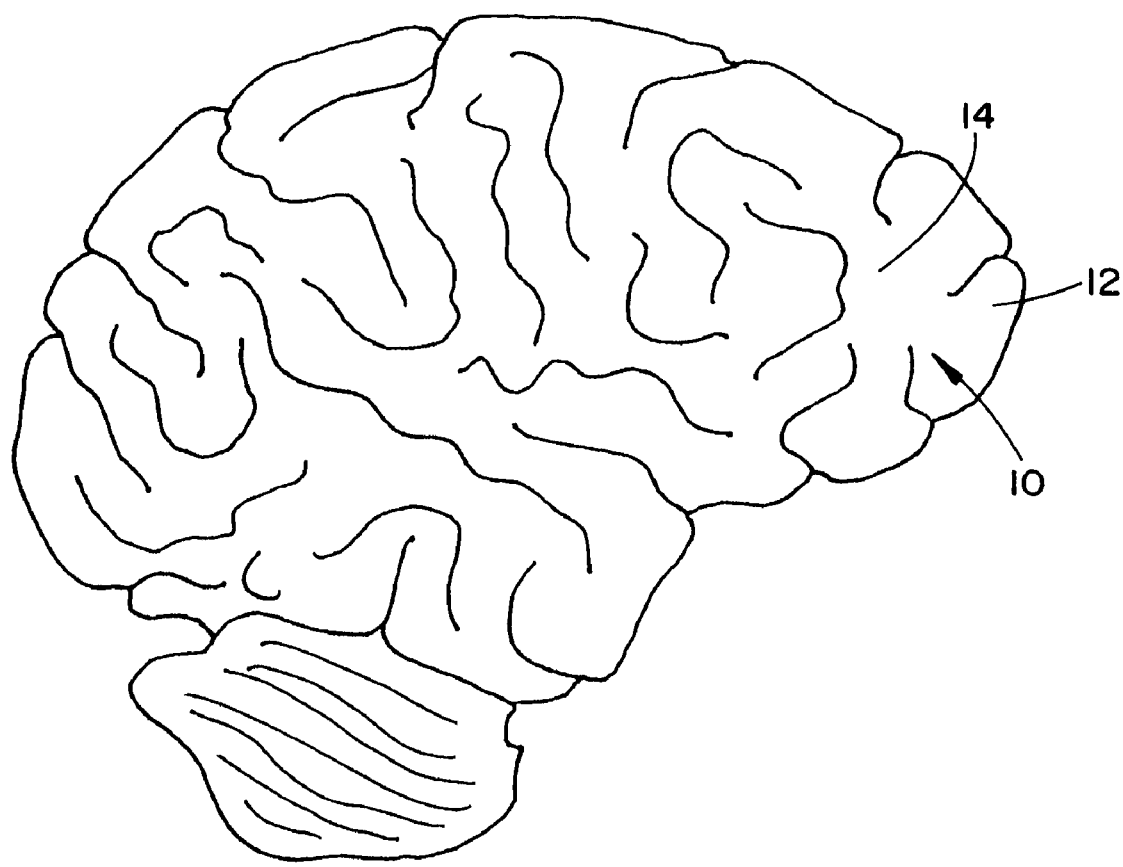
FIG. 1 is a schematic isometric view of the cerebral cortex, wherein the inferior frontal gyrus is identified.
Figure 2:
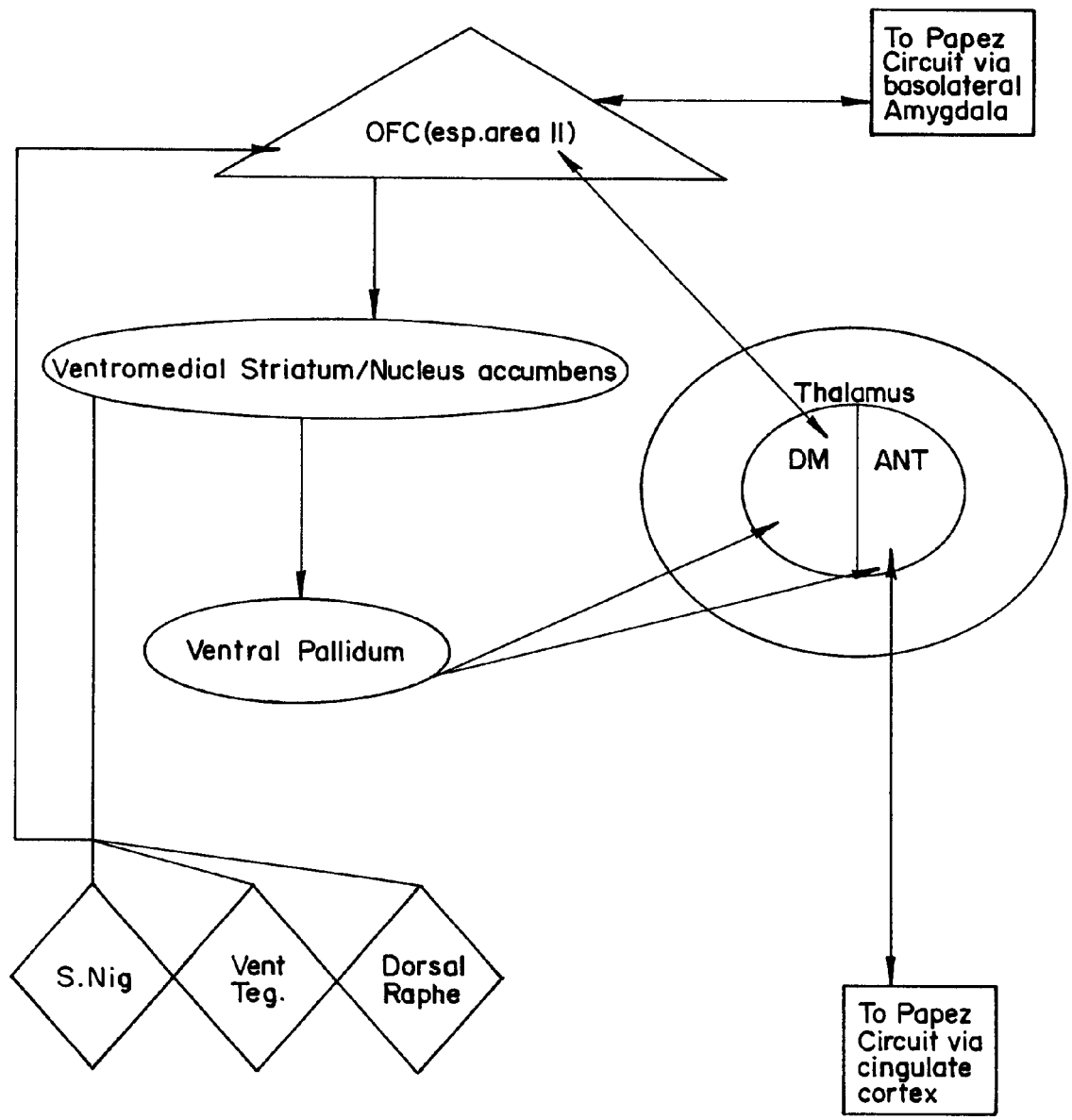
FIG. 2 is a conceptual map of the circuitry of the human brain, specifically with respect to the accepted model for activity relating to certain psychiatric disorders.
Figure 3:
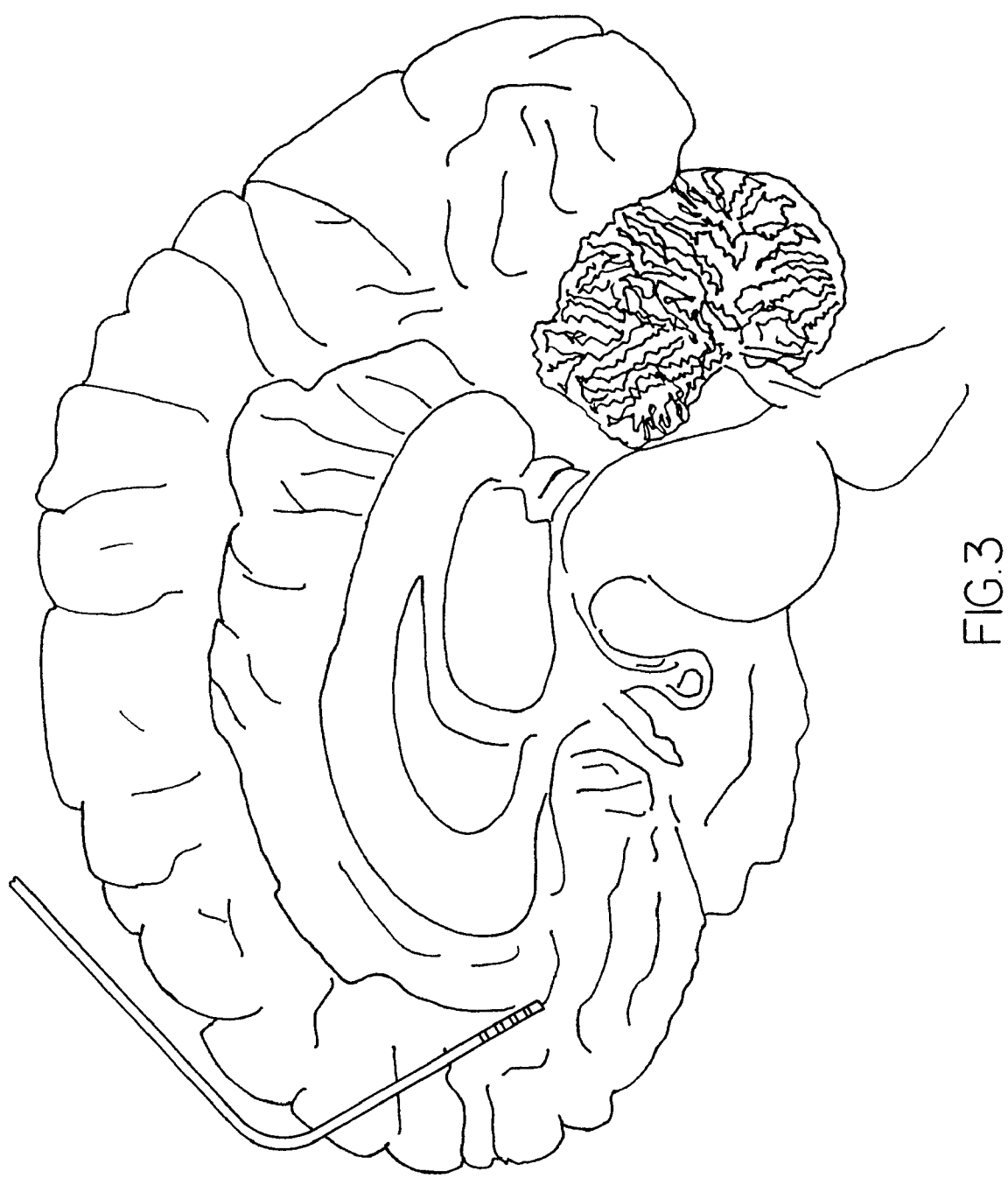
FIG. 3 is a side cross-section view of a human brain having a stimulation electrode implanted within the OFC in accordance with a method that is an aspect of the present invention.
Figure 4:
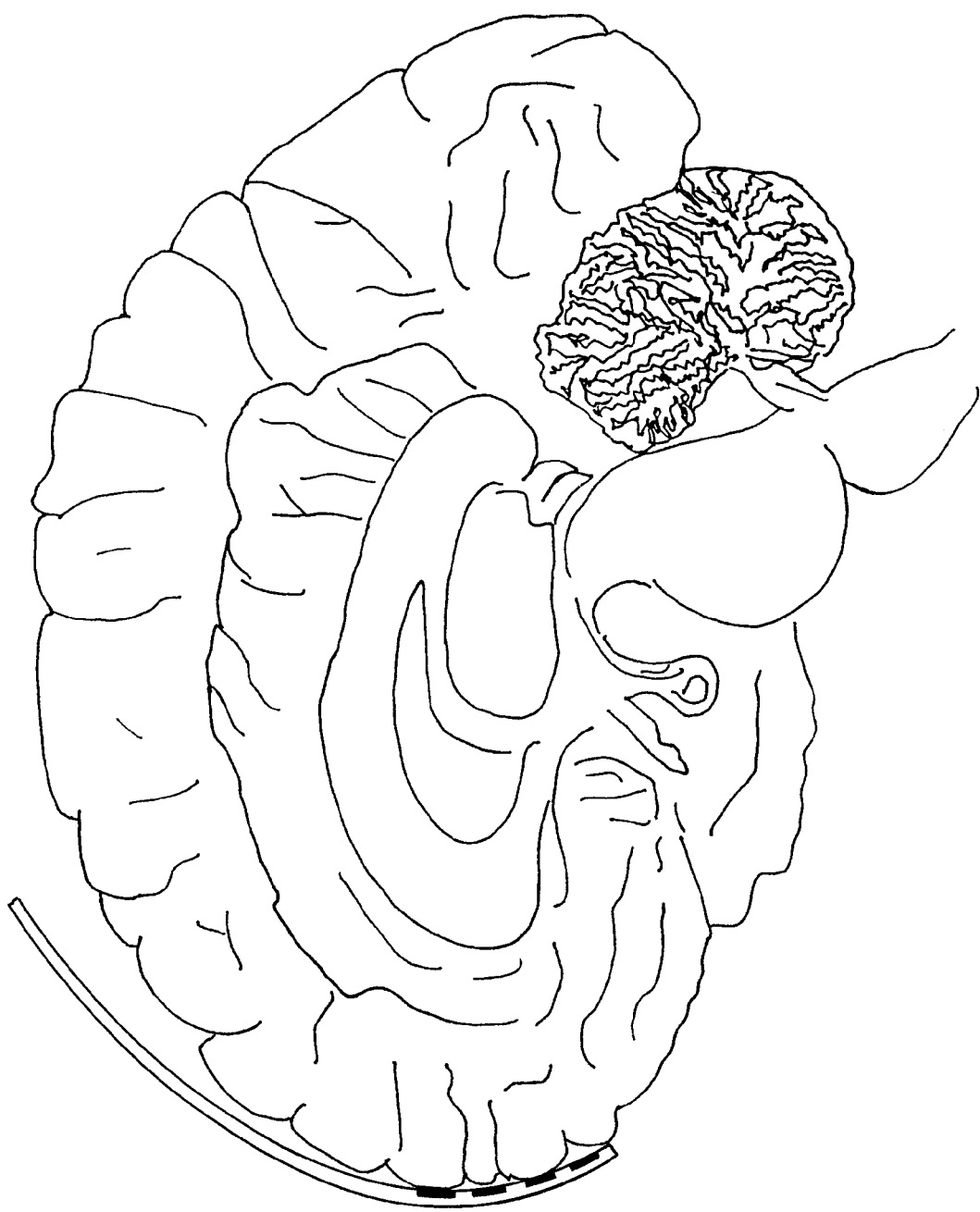
FIG. 4 is a side cross-section view of a human brain having a stimulation electrode implanted epidurally and/or subdurally at the OFC in accordance with a method which is an aspect of the present invention.
Figure 5:
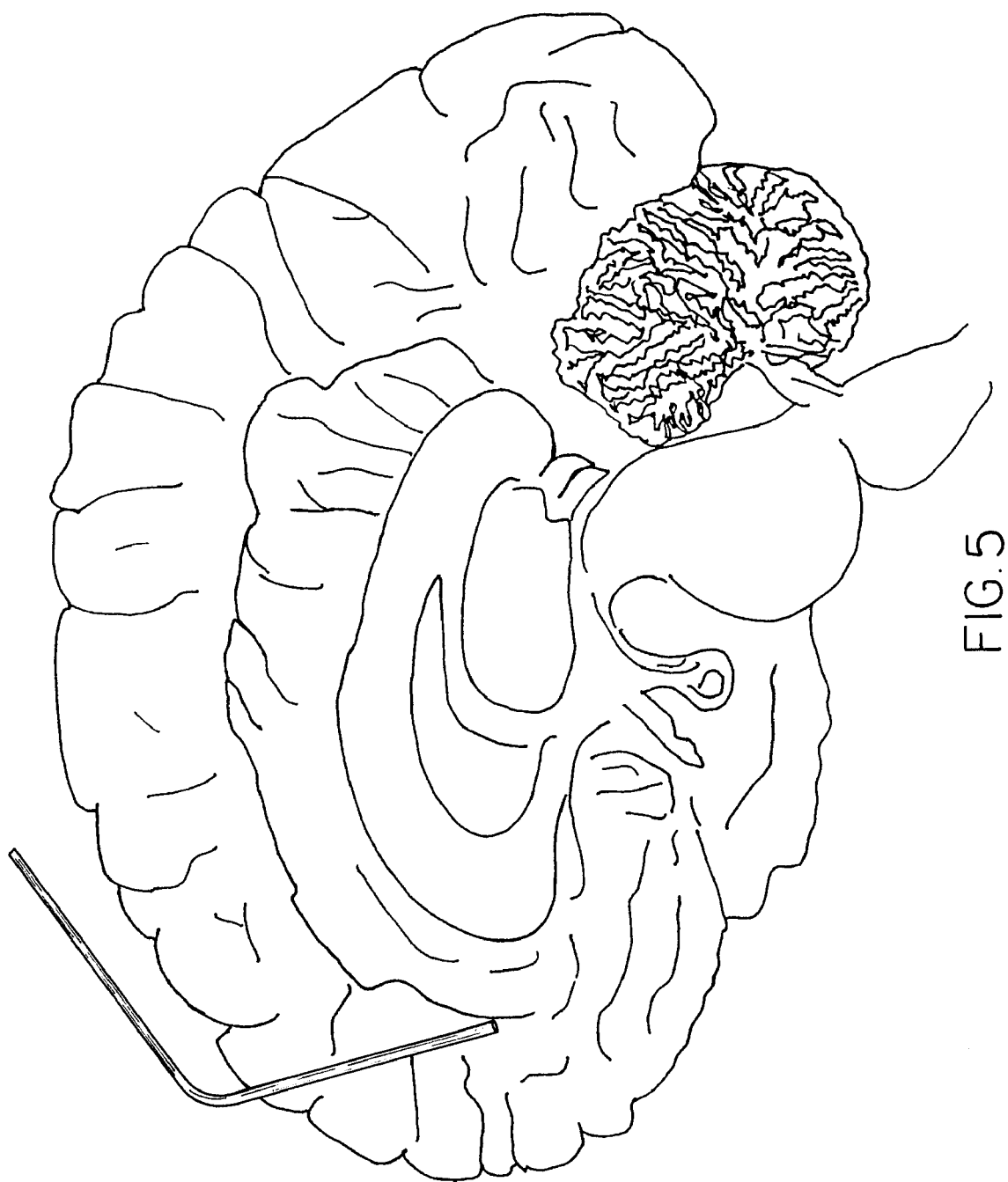
FIG. 5 is a side side cross-section view of a human brain having a catheter implanted within the OFC in accordance with a method which is an aspect of the present invention.

Surgical intervention comprises the second stage of the treatment. It is the specific use of the electrical stimulator and/or drug-delivery catheter, for treatment of psychiatric disorders which comprises the inventive step in the present method, and not the implantation technique itself. More particularly, the standard neurosurgical techniques for implantation of an electrical stimulation device and/or drug delivery device into the brain may be utilized. In fact, referring to FIGS. 3, 4 and 5, in which a side cross-section of a human brain having the aforementioned types of stimulation is provided, it shall be understood that the impantation of electrodes and or catheters into various regions of the brain, specifically the OFC is known. In particular, FIG. 3 shows a stimulation electrode implanted within the OFC in accordance with a method that is an aspect of the present invention. FIG. 4 shows the stimulation electrode implanted epidurally (subdurally) to the OFC. FIG. 5 shows a catheter implanted within the OFC. It is the application of this technique for the treatment of psychiatric disorders which has not previously been described. This technique, therefore, is as follows.

Patients who are to have an electrode and/or catheter implanted within the OFC, first have a steroetactic head frame, such as the Leksell, CRW, or Compass, is mounted to the patient's skull by fixed screws. Subsequent to the mounting of the frame, the patient undergoes a series of magnetic resonance imaging sessions, during which a series of two dimensional slice images of the patient's brain are built up into a quasi-three dimensional map in virtual space. This map is then correlated to the three dimensional stereotactic frame of reference in the real surgical field. In order to align these two coordinate frames, both the instruments and the patient must be situated in correspondence to the virtual map. The head frame is therefore rigidly mounted to the sugical table. Subsequently, a series of reference points are established relative aspects of the frame and patient's skull, so that the computer can adjust and calculate the correlation between the real world of the patient's head and the virtual space model of the patient MRI scans. The surgeon is able to target any region within the stereotactic space of the brain within 1 millimeter precision. Initial anatomical target localization is achieved either directly using the MRI images, or indirectly using interactive anatomical atlas programs which map the atlas image onto the steroetactic image of the brain. In the present invention, the target space is that occupied by the orbitofrontal cortex.

One form of the surgical aspect of the invention involves the placement of an electrode and/or drug-delivery cathter within the OFC substance itself. This surgery can be performed under either local or general anaesthetic. An initial incision is made in the scalp, preferably 3–4 centimeters lateral to the midline of the skull, anterior to the coronal suture. A burr hole is then drilled in the skull itself; the size of the hole being suitable to permit surgical manipulation and implantation of the electrode. This size of the hole is generally about 14 millimeters. The dura is then opened, and a fibrin glue is applied to minimize cerebral spinal fluid leaks and the entry of air into the cranial cavity. A guide tube cannula with a blunt tip is then inserted into the brain parechyma to a point approximately one centimeter from the target tissue. At this time physiological localization starts with the ultimate aim of correlating the anatomical and physiological findings to establish the final stereotactic target structure.

Physiological localization using single-cell microelectrode recording is preferable for definitive target determination. Sole reliance on anatomical localization can be problematic because of the possible discrepancies between the expected location (expected from the visualization provided by the virtual imaging of the MRI) and the actual position within the skull. Microelectrode recording povides exquisite physiological identification of neuronal firing patterns via direct measures of individual single unit neuronal acitivity. Single-cell microelectrode recordings obtained from intralaminar thalamic cells typically have a characteristic bursting activity. In addition to microelectrode recording, microstimulation and or macrostimulation may be performed to provide further physiological localization.

Once the final target nuclei have been identified in the real spatial frame of reference, the permanent electrode and/or drug-delivery catheter is implanted. General principles guiding the final implantation of an electrode involve the placement of the electrode in a, region, and in an orientation, allowing for maximal efficacy while minimizing the undesired side effects. The currently used brain stimulating electrodes are quadripolar electrodes. The electrode itself is approximately 1–1.5 millimeter diameter flexible elastomeric sheath which contains four wound wire leads. The leads terminate at the distal and proximal ends of the sheath in four electrically insulated cylindrical contact pad. The contact pads at the distal end are less than 2 millimeters in length and are separated by an insulating distance, for example between 0.5 and 2 millimeters. At the proximal end, which is anywhere from 25 to 50 centimeters distance from the distal end, a corresponding series of contacts are provided so that the electrode may be coupled to a potential source, or to a coupling lead which permits remote disposition of the signal source.

The drug delivery cathter is a silastic tube similar to the one used in the intrathecal drug delivery systems commonly in use. With regard to catheter placement, care is taken not to place the catheter directly within a vascular structure. This can be achieved by combing data from conventional and/or magnetic resonance angiography into the stereotactic targeting model. The distal portion of the cathter has multiple orifices to maximize delivery of the agent while minimizing mechanical occlusion. The proximal portion of the catheter can be connected directly to a pump or via a metal and/or plastic hollow connector, to an extending cathter.

The second aspect of the invention involves the placement of an electrode and/or drug-delivery catheter epidurally and/or subdurally in the region of the OFC. This is also a stereotactic procedure done either under local or general anaesthesia. In this case, however, a frameless based stereotactic system is used (SMN, Steatlth, Cygnus etc.). In these systems, fiducials, a type of marker, is placed on the patient's scalp prior to preoperative imaging studies. These markers form a virtual frame around which the stereotactic targeting model is built. Next, curivlinear incision is made behind the hairline, approximately 0.5 cm anterior to the pinna, extending from the root of the zygoma to the midline. Next, a limited "pterional-type" craniotomy is fashioned with particular care in gaining access to the orbital surface of the frontal lobe. The electrodes could then be placed in the epidural and/or subdural space and secured with non-absorbable suture. The drug catheter would be placed in the subdural and ideally the subarachnoid space. Further intraoperative physiological localization measures would proceed as above.

The initial application of the electrical signal through the electrode is then attempted. The range of signal types are between 0.1 to 20 volts, with a pulse width of 10 microseconds to 1000 microseconds, and a frequency of 2 to 2500 Hertz. The stimulation can be monopolar or bipolar depending upon the specific relative potentials applied to the electrical contacts relative to the patient's tissue. Various stimulation parameters are tested to assess side effects (such as motor contraction, paresthesias, visual disturbance, pain, and autonomic modulation) or clinical efficacy. With regard to a chemical based system, the drug-delivery pump may be programmed with an initial nominal dose scheme. Psychiatric disorders treated by electrostimulation and/or pharmacotherapy, however, may take up to six months to demonstrate clinical efficacy. Long term adjustment of the signal and/or dosage being applied by the power source and/or drug-delivery pump may be required to optimize the outcome. If the patient's symptoms do not subside, the surgeon will attempt to adjust all of the parameters until they do.

As is readily obvious to anyone who has witnessed the unnecessary surgical procedure associated with the remote localization of the power source and/or drug-delivery system, it is desirable the burr cap structure itself comprise the signal and/or drug source. However, as that option is not presently available the signal source generator and/or drug-delivery system must be disposed at a remote site in the patient's body. A specially designed plastic cap is generally provided to seat in the burr hole, and permit the proximal end of the electrode to pass out through the skull. The incision in the patient's skull is then sutured closed with the electrode temporarily stored under the skin. If the patient is not already under general anaesthesia, the patient is so disposed and a tunnel is formed under the dermal layers, connecting the incision in the scalp to the remote location for the signal generator and/or drug pump (usually the infraclavicular region, beneath the collar bone—where cardiovascular pace makers are implanted or the paraumbilical region). Subsequent joining of the electrode and/or catheter to a coupling (extending) lead and/or cathteter from the signal source and/or drug-delivery pump to the brain electrode and/or cathter is then necessary, however, generally the manner in which the electrode and/or cathter and the extending lead and/or catheter are coupled utilizes the same terminal contacts and/or connections as would be used for direct coupling to the power source and or drug-delivery system.

Once the sugery is complete, a non-contrast CT scan is taken to ensure that there is no intracranial hematoma. Subsequently, various stimulation parameters are programmed and patients are assessed for any side effects as well as clinical efficacy. As behavioral and related cognitive improvement may not occur immediately, long-term benefits may not be achieved until multiple adjustments are accomplished.

While there has been described and illustrated specific embodiments of new and novel methods of treatment for psychiatric disorders, it will be apparent to those skilled in the art that variations and modifications are possible without deviating from the broad spirit and principle of the present invention which shall be limited solely by the scope of the claims appended hereto.

We claim:

1. A method of determining the proper therapeutic treatment for, and subsequently treating a specific psychiatric disorder comprising the steps of:

identifying a large sampling of patients, each exhibiting a common specific psychiatric disorder;

identifying which common region of the frontal cerebral cortex exhibits pathological electrical during manifestations of the specific psychiatric disorder, said common region thereafter constituting a predetermined treatment site;

surgically implanting an electrode in the brain of each of said patients so that a distal end thereof lies in communication with the predetermined treatment site in the frontal cortex of the brain;

coupling a proximal end of said electrode to an electrical signal source; and operating said electrical signal source to stimulate said predetermined treatment site in the frontal cortex of the brain, whereby the effects of psychiatric disorder are reduced.

2. The method as set forth in claim 1, wherein operating said electrical signal source to stimulate said predetermined treatment site in the frontal cortex of the brain comprises operating said electrical signal source to increase frontal cortex activity at said predetermined treatment site.

3. The method as set forth in claim 1, wherein operating said electrical signal source to stimulate said predetermined treatment site in the frontal cortex of the brain comprises operating said electrical signal source to decrease frontal cortex activity at said predetermined treatment site.

4. The method as set forth in claim 1, wherein said psychiatric disorder is selected from the group consisting of Anxiety Disorder, Affective Disorder, and Substance Abuse Disorder.

5. The method as set forth in claim 1, wherein the common regions of the frontal cerebral cortex constituting the predetermined treatment site is the orbitofrontal cortex.

* * * * *